United States Patent [19]

Myers et al.

[11] Patent Number: 5,032,526

[45] Date of Patent: Jul. 16, 1991

[54] METHOD FOR THE COLORIMETRIC DETERMINATION OF SULFONATES IN AQUEOUS SYSTEMS

[75] Inventors: Ronald R. Myers, Coraopolis; Jack E. Fink, Darlington, both of Pa.

[73] Assignee: Calgon Corporation, Pittsburgh, Pa.

[21] Appl. No.: 463,647

[22] Filed: Jan. 11, 1990

Related U.S. Application Data

[62] Division of Ser. No. 540,330, Oct. 11, 1983, Pat. No. 4,894,346.

[51] Int. Cl.$^5$ ................. G01N 21/78; G01N 33/44
[52] U.S. Cl. ........................ 436/85; 436/120; 436/164; 436/175; 436/177
[58] Field of Search ................. 436/85, 119, 120, 164, 436/175, 177, 178

[56] References Cited

U.S. PATENT DOCUMENTS

| | | |
|---|---|---|
| 3,490,874 | 1/1970 | Ando et al. |
| 3,969,076 | 7/1976 | Wang .................. 436/163 |
| 3,992,149 | 11/1976 | Wang .................. 436/164 |
| 4,141,688 | 2/1979 | Morris et al. |
| 4,290,776 | 9/1981 | Yamada |
| 4,318,709 | 3/1982 | Falb et al. |

FOREIGN PATENT DOCUMENTS

| | | |
|---|---|---|
| 540209 | 12/1976 | U.S.S.R. |
| 0702279 | 12/1979 | U.S.S.R. .................. 436/120 |
| 709985 | 1/1980 | U.S.S.R. |
| 777571 | 11/1980 | U.S.S.R. |
| 0769429 | 12/1980 | U.S.S.R. .................. 436/120 |
| 1027610 | 7/1983 | U.S.S.R. .................. 436/120 |
| 1195149 | 3/1985 | United Kingdom . |

OTHER PUBLICATIONS

Swett et al, Analytical Chemistry, vol. 38, No. 13, pp. 1958-1959.

Klyachko et al, Chemical Abstracts, vol. 76, Entry No. 154343V, p. 15.

Patent abstracts of Japan, vol. 5, No. 175 (p-88).

*Primary Examiner*—Robert J. Hill, Jr.
*Attorney, Agent, or Firm*—W. C. Mitchell; J. F. DiPrima

[57] ABSTRACT

The instant invention is directed to a method for determining the concentration of sulfonate and/or polycarboxylate compounds in an aqueous solution comprising:

(a) adjusting the pH of a portion of the aqueous solution to less than 3.0 when measuring sulfonate concentration or to between 3.0 and 12.0 when measuring polycarboxylate concentration;

(b) adding an effective amount of an aqueous solution containing a metachromatic dye to the pH-adjusted portion of Step (a);

(c) measuring the absorbance of the admixture resulting from Step (b) at a wavelength between 300 nm and 700 nm; and (d) comparing the absorbance from Step (c) with absorbances of standard samples containing known concentrations of sulfonate and/or polycarboxylate compounds and said effective amount of the dye solution of Step (b), thereby determining the sulfonate and/or polycarboxylate concentration of the portion of Step (a).

10 Claims, 4 Drawing Sheets

METHOD FOR THE COLORIMETRIC DETERMINATION OF SULFONATES IN AQUEOUS SYSTEMS

This is a division of application Ser. No. 540,330, filed Oct. 11, 1983, now U.S. Pat. No. 4,894,346.

BACKGROUND OF THE INVENTION

Water has a number of important industrial uses, including its use as a medium to remove heat from process equipment and its use in the generation of steam. Unfortunately, untreated water cannot be used directly for these or other purposes in most instances due to the presence of various impurities which may prevent effective heat transfer, interfere with fluid flow, or corrode process equipment. In such cases, treatment of the water is required to assure efficient equipment operation. For example, compounds which inhibit scale formation are commonly added to cooling tower and boiler waters to prevent the formation or deposition of scale on equipment in contact with these waters.

Most industrial waters contain metal cations, such as calcium, barium, magnesium, and sodium and anions, such as bicarbonate, carbonate, sulfate, phosphate, silicate, and fluoride. When combinations of these anions and cations are present above certain concentration limits, reaction products precipitate on the surfaces of equipment in the system containing the water, forming scale or deposits. This precipitation is an expensive problem in many industrial water systems, causing delays and shutdowns for cleaning and removal.

Formation of scale compounds can be prevented by insuring that the solubility limits of cation-anion reaction products are not exceeded. Certain water-soluble polymers, including polymers derived from unsaturated carboxylates and unsaturated sulfonates, or their salts, are useful for this purpose. When these polymers are added to industrial waters to inhibit scale, their concentrations must be frequently determined to properly monitor system performance. If too little of a polymer is present, the system may not be adequately protected; if too much of a polymer is present, the treatment may not be cost effective. For a given system, there is an optimal treatment concentration which must be maintained. It is therefore desirable to be able to quickly and accurately determine the concentration of treatment chemicals in water systems.

GENERAL DESCRIPTION OF THE INVENTION

The present invention relates to a method for determining the concentration of polycarboxylates and/or sulfonates in aqueous systems. More particularly, it relates to a test method for determining the concentration of polycarboxylate and/or sulfonate compounds in industrial water systems, including but not limited to boilers, cooling towers, evaporators, gas scrubbers, kilns and desalination units, which correlates the intensity of color developed in the reaction between polycarboxylate and/or sulfonate molecules and various dyes to the concentration of these components in the aqueous system.

Colorimetry is a well-known method of chemical analysis which involves the comparison and matching of a standard color with that of an unknown one to approximate the concentration of a specific component in the unknown sample. Because the amount of light absorbed by a given substance in solution is proportional to the concentration of the absorbing species, colorimetry is a simple and accurate method for determining unknown concentrations. For example, if the concentration of a polymer in an aqueous system must be determined, a sample can be taken; the absorbance of the sample in the presence of a suitable dye can then be measured and compared with a calibration curve to quickly and accurately estimate the concentration of the polymer in the aqueous system. This mode of testing is advantageous in that it can easily be performed at the application site.

The Applicants have discovered that certain metachromatic dyes are suitable for use in colorimetrically determining the concentration of polycarboxylates and sulfonates in aqueous systems. The method disclosed herein is particularly well suited for quickly and accurately determining the concentrations of polycarboxylate and/or sulfonate corrosion or scale inhibitors in aqueous systems, including but not limited to boilers, cooling towers, evaporators, gas scrubbers, kilns and desalination units.

Certain dyes undergo a unique color change upon interaction with polyionic compounds in solution. This color change, known as metachromaticity, is the basis for the colorimetric method disclosed herein. When anionic polymers contact a metachromatic dye, the dye molecules align with the anionic charges on the polymers, resulting in a shift in the wavelength of maximum absorbance of the dye molecule. This shift is observable as a color change in the solution containing the dye and the polymer. Since polycarboxylates and sulfonates, which are anionic, induce a metachromatic change in certain dyes, their concentrations in aqueous solutions can be determined colorimetrically by measuring the absorbance, at a specified wavelength, of a solution containing polycarboxylates and/or sulfonates and a metachromatic dye and comparing this absorbance to absorbances of standards having known concentrations of the species being measured.

Selectively, as used herein, relates to the ability of a test method to differentiate between different species in the sample solution. The selectivity of this test method is excellent between sulfonates and polycarboxylates due to their relative acid strengths. At low pH's, for example less than 3.0, relatively few carboxylic acid groups have charges since they are largely associated with hydrogen ions, while sulfonic acid groups, being stronger acids than carboxylics, are ionized at pH's as low as 2.5. Sulfonic acid groups can therefore induce metachromatic color changes at pH's less than 3.0, while carboxylic acid groups generally do not. At pH's greater than 3.0, both carboxylic and sulfonic acid groups induce metachromatic changes in certain dyes. This allows a skilled chemist to determine the concentrations of sulfonates alone, or sulfonates and polycarboxylates, by using a suitable metachromatic dye and measuring absorbances at the proper pH and wavelength.

The test method of the instant invention is also selective in that anions most commonly found in water samples, for example $Cl^-$, $HCO_3^-$ and $SO_4^-$, among others, do not significantly alter the metachromaticity of dye molecules.

DETAILED DESCRIPTION OF THE INVENTION

Figure 1:
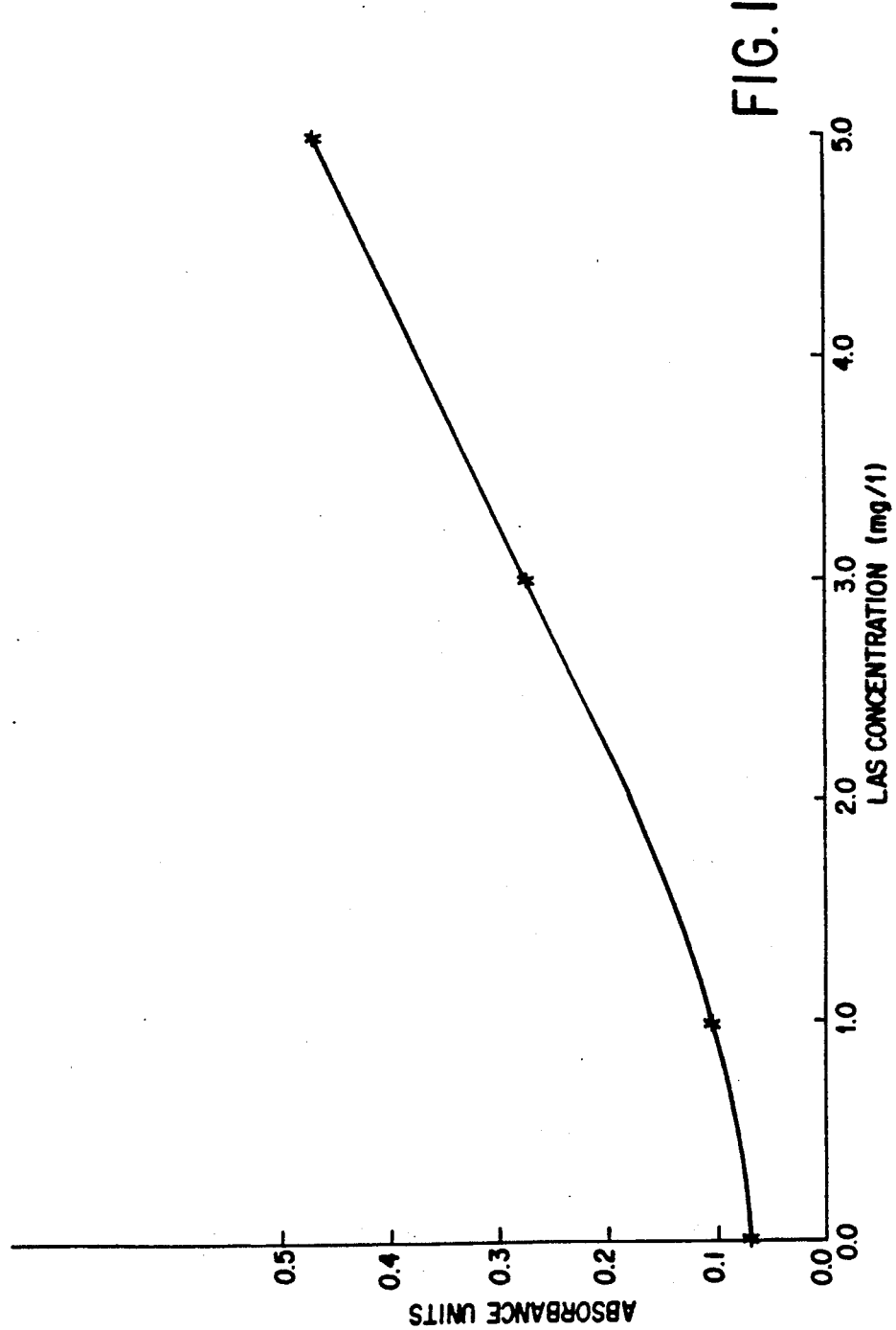
FIG. 1 shows the relationship between absorbance and sulfonate concentration, as determined by the method described in Example 1.

The instant test method for determining the concentration of polycarboxylate and/or sulfonate compounds in an aqueous solution comprises:
(a) adjusting the pH of a portion of the aqueous solution to less than 3.0 when testing for sulfonates or to between 3.0 and 12.0 when testing for polycarboxylates;
(b) adding an effective amount of an aqueous solution of a metachromatic dye to the pH-adjusted portion or sample of Step (a), wherein an effective amount refers to an amount of said dye solution which will, when added to the portion of Step (a), result in a dye to polycarboxylate group and/or sulfonate group mole ratio between 0.1 and 100 in the admixture;
(c) measuring the absorbance of the admixture resulting from Step (b) at a wavelength between 300 nm and 700 nm;
(d) comparing the absorbance from Step (c) with absorbances of standard samples containing known concentrations of polycarboxylate compounds and/or sulfonate compounds and said effective amount of the dye solution of Step (b), thereby determining the sulfonate and/or polycarboxylate concentration of the portion of Step (a).

Polycarboxylates include polymers produced from any unsaturated carboxylic acid or salt thereof, including but not limited to acrylic acid, methacrylic acid, maleic acid, itaconic acid, vinylacetic acid, allyl acetic acid, fumaric acid, phosphinocarboxylic acid, and B-carboxyethyl acrylate, alone or in combination.

Sulfonates include polymers produce from any unsaturated sulfonic acid or salt thereof, including but not limited to 2-acrylamido-2-methylpropyl sulfonic acid, 2-methacrylamido-2-methylpropyl sulfonic acid, styrene sulfonic acid, vinyl sulfonic acid, sulfo acrylate or methacrylate, allyl sulfonic acid, methallyl sulfonic acid, 3-methacrylamido-2-hydroxy propyl sulfonic acid and sulfonic acid acrylate, alone or in combination.

Polycarboxylates and sulfonates, as used herein, also include polymers produced by combining any unsaturated carboxylic acid, or salt thereof, with any unsaturated sulfonic acid, or salt thereof.

The method disclosed herein is especially effective when the species to be measured is a water-soluble polycarboxylate which is used as a scale inhibitor, such as a polymer made using acrylic acid, alone or in combination with acrylamide or other monomers, or hydrolyzed polymers of acrylamide. The method disclosed herein is also especially effective when the species to be measured is a water-soluble polysulfonate which is used as a scale inhibitor, such as a copolymer made using an unsaturated carboxylic monomer and an unsaturated sulfonate monomer, wherein the ratios of the respective monomers range from 99:1 to 1:99.

The portion or sample of Step (a) may be any convenient amount of the aqueous solution containing polycarboxylate and/or sulfonate compounds. Also, pretreatment of the sample or portion of Step (a) may be desirable. Examples of pretreatment steps include: filtration of the sample or portion to remove particulates; addition of an effective amount of a reducing agent to reduce chlorine and/or ferric iron, if present, in the sample or portion, thereby minimizing interference from these components; dilution of the sample or portion to bring the concentration of the component being measured in the sample or portion within the concentration range of standard sample; and adding an effective amount of thorium to the sample or portion to eliminate or minimize hexametaphosphate interference. Hexametaphosphate interference may also be minimized by the addition of an effective amount of an acid to the sample or portion followed by boiling.

The preferred pH range for polycarboxylates is 6.5 to 7.5, and the preferred pH range for sulfonates is 2.4 to 2.6. Many suitable agents for pH adjustment are known to those skilled in the art, including but not limited to chloroacetic acid/sodium chloroacetate, $KH_2PO_4$/NaOH, potassium-hydrogen phthalate/hydrochloric acid and sodium bicarbonate/sodium hydroxide buffer solutions.

Any metachromatic dye can be used in a colorimetric test to determine the polycarboxylate and/or sulfonate concentrations in an aqueous solution. Metachromatic dyes are those which undergo a color change upon interaction with polyionic compounds. Examples of metachromatic dyes include, but are not limited to, crystal violet, methyl green, malachite green, acridin organge and paraosaniline. Metachromatic dyes selected from the group consisting of nile blue A, neutral red, safrin O, methyl blue, methyl red, toluidine blue, new methylene blue, quinalizarin, tetrachrome, brilliant blue G, mordant black II and pinacyanol chloride, have been found by the inventors to be most suitable for use in a colorimetric test to determine polycarboxylate and/or sulfonate concentrations in aqueous systems. The preferred dyes are nile blue A and pinacyanol chloride. The most preferred dye is pinacyanol chloride. For any metachromatic dye used, the mole ratio of dye molecules to sulfonate and/or polycarboxylate groups should be between 0.1 and 100.0.

The preferred dye concentration is between $1 \times 10^{-6}$M and $1 \times 10^{-1}$M. However, since the "effective amount" referred to in Step (b) refers to the ratio of moles of dye to the moles of sulfonate and/or polycarboxylate groups in the admixture of Step (b), and since the effective amount of dye must result in an absorbance between 0.01 and 2.0 as measured on a spectrophotometer, tradeoffs exist between the concentration of the dye solution used, the quantity of the dye solution added, and length of light path (i.e. the cell length) used to measure absorbance. For example, as the length of light path decreases, the moles of dye molecules present in the admixture of Step (b) should be increased. This can be accomplished by either using dye solution of higher concentration or by adding more of a dye solution of lower concentration. It is within the reach of the skilled chemist to balance these variables so as to obtain an absorbance between 0.01 and 2.0 on the spectrophotometer used.

Absorbance, as used herein, may be defined according to the Lambert-Beer Law as follows:

$$A = abc,$$

where
A = absorbance,
a = absorbtivity of the dye,
b = light path length, and
c = concentration of the colored substance.

Each dye used will have a range of maximum absorbance within the 300 to 700 nm range, and it is desirable to measure absorbance at a wavelength within this range of maximum absorbance. Any spectrophotometer may be used. The preferred wavelength for determining the concentration of sulfonates is 480 to 490 nm when pinacyanol chloride is the dye, and the preferred wavelength for determining the concentration of polycarboxylates is 590 to 640 nm when pinacyanol chloride is the dye. The preferred wavelength for determining the concentration of polycarboxylates or sulfonates is 630 to 640 when nile blue A is the dye.

An effective amount of an aqueous solution of a metachromatic dye, in addition to being an amount which will, when added to the portion of Step (a), result in a dye to polycarboxylate group and/or sulfonate group mole ratio between 0.1 and 100, should preferably result in an absorbance between 0.01 and 2.0 on the spectrophotometer used, thereby placing the spectrophotometer "on scale".

Standard samples containing known concentrations of sulfonates and/or polycarboxylates and an effective amount of dye should be prepared for comparison purposes. For example, if sulfonate concentration is to be measured in an aqueous system, samples containing known concentrations of the sulfonate to be measured should be prepared. The concentration range of the standard samples should include the expected or possible concentration range of the unknown sample. An effective amount of a metachromatic dye should then be added to each standard sample and to the unknown sample or portion. The effective amount of dye solution added to each standard sample should be equivalent to the effective amount of dye solution added to the unknown sample or portion, and each standard sample should be equal in volume to the unknown sample or portion. Absorbance of the standard samples and of the unknown sample should then be measured. By comparison of the absorbance of the unknown sample to those of the standard samples, concentration of the sulfonate in the unknown sample can be estimated.

EXAMPLES

The following examples are provided to further teach the method of the present invention. Thus, preferred embodiments are described and analyzed. The examples are meant to illustrate only, and are in no way intended to limit the scope of the invention described and claimed herein.

EXAMPLE 1

Preparation of Colorimetric Standards—Sulfonates with Pinacyanol Chloride

A linear alkyl benzene sulfonate (LAS) stock solution was prepared by diluting 0.117 g of an Environmental Protection Agency (EPA) LAS reference standard solution containing 5.97 percent LAS to 100 ml with water. From this LAS stock solution were prepared LAS standards containing 1.0, 3.0 and 5.0 mg/l LAS by diluting 1.43, 4.29 and 7.15 ml of the stock solution to 100 ml with water. To 5.0 ml of each of the LAS standards and to 5.0 ml of deionized water were added 0.05 g of ascorbic acid and 0.50 ml of a buffer solution consisting of 2M chloroacetic acid, 1M sodium chloroacetate and 60 mg/l thorium. The resulting pH was 2.2. Twelve and one-half ml of a $9 \times 10^{-5}$M aqueous solution of pinacyanol chloride were then added to each of these four solutions. The resulting mole ratios of dye molecules to sulfonate groups were 70.0, 23.0, 14.0, and 0.0 (deionized water). The intensity of the blue color developed was measured for each standard at a wavelength of 485 nm in a 50 mm (light path length) cell using a Bausch & Lomb/Shimadzu Spectronic 200 uv spectrophotometer. A calibration curve of absorbance versus LAS concentration was prepared and is shown as FIG. I.

EXAMPLE 2

Determination of Sulfonate Concentrations In River Water Using Pinacyanol Chloride A 5.0 ml sample of a filtered river water containing 4.0 mg/l of LAS was prepared using the EPA reference standard solution of Example 1. To the sample were added 0.05 g of ascorbic acid and 0.50 ml of a buffer solution consisting of 2M chloroacetic acid, 1M sodium chloroacetate and 60 mg/l thorium. The resulting pH was 2.2. Twelve and one-half ml of a $9 \times 10^{-5}$M aqueous solution of pinacyanol chloride were added to the treated river water sample. The intensity of the blue color developed was measured at a wavelength of 485 nm in a 50 mm cell (light path length) using the spectrophotometer of Example 1. The absorbance was 0.38 absorbance units. Comparison of the sample absorbance with the absorbances of LAS standards shown in FIG. I indicated an LAS concentration of approximately 4.1 mg/l in the river water. The error of 0.1 mg/l is within the expected 10 percent accuracy range of the test.

EXAMPLE 3

Preparation of Colorimetric Standards—Acrylates With Pinacyanol Chloride

Figure 2:
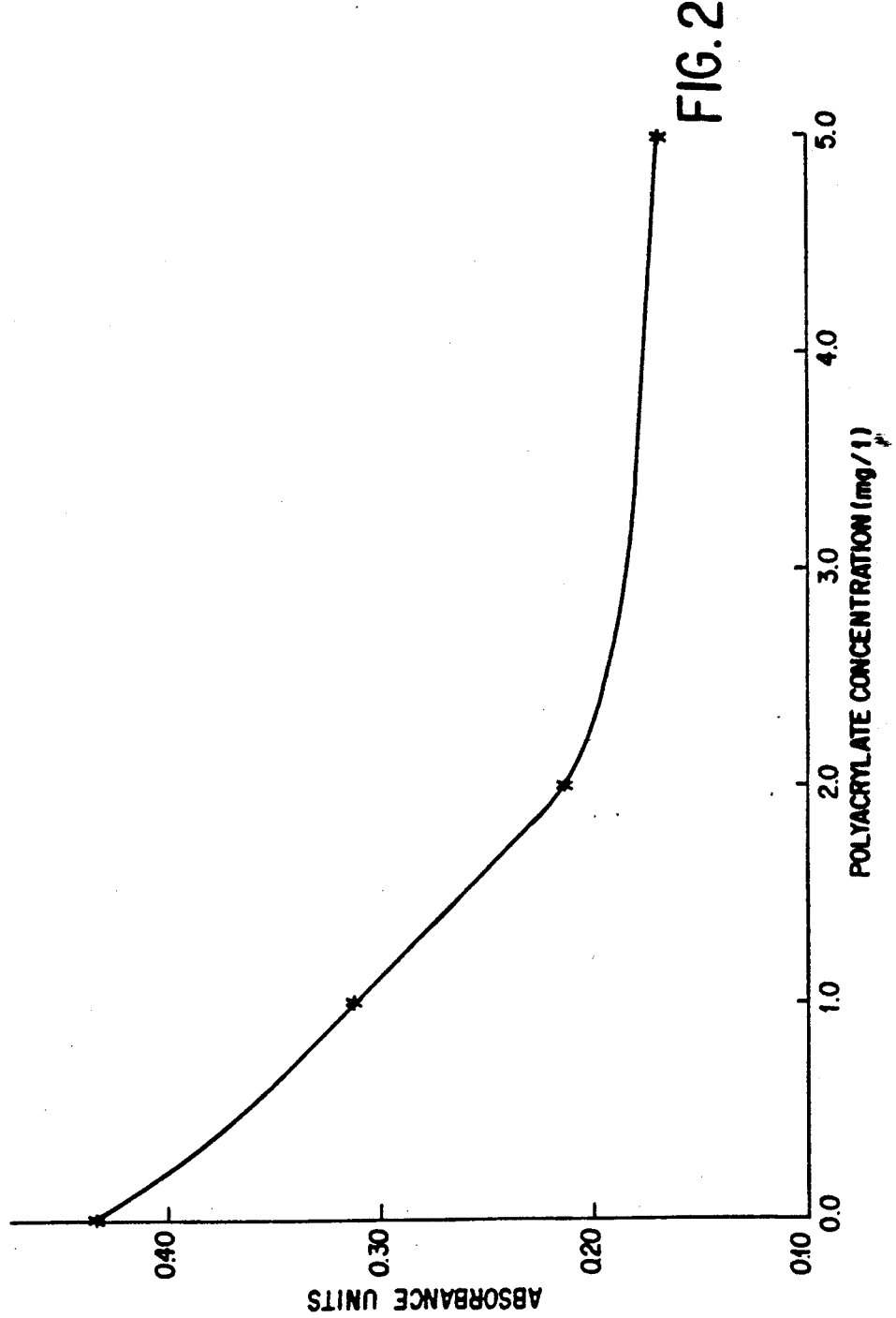
FIG. 2 shows the relationship between absorbance and polyacrylate concentration, as determined by the method described in Example 3.

Polyacrylate standards containing 1.0, 2.0 and 5.0 mg/l of a commercially available polyacrylate having a molecular weight between 2000 and 3000 were prepared by diluting a 1000 mg/l polyacrylate analytical standard solution available from Calgon Corporation with water. To 10.0 ml of each o the above standards and to 10.0 ml of deionized water were added 1.0 ml of a buffer solution consisting of 0.062M KH$_2$PO$_4$ and 0.038M NaOH. The resulting pH was 6.8. Two ml of a $9 \times 10^{-5}$M aqueous solution of pinacyanol chloride were then added to each of these four solutions. The resulting mole ratios of dye molecules to carboxylic acid groups were 1.3, 0.6, 0.3 and 0.0 (deionized water). The intensity of the resultant color was measured for each standard in a 1 cm cell (light path length) at 600 nm using the spectrophotometer of Example 1. A calibration curve of absorbance versus polyacrylate concentration was prepared and is shown as FIG. 2.

EXAMPLE 4

Determination of Polyacrylate Concentration In An Industrial Cooling Tower Makeup Water Using Pinacyanol Chloride A filtered cooling tower makeup water sample containing 10 mg/l polyacrylate was prepared using the polyacrylate analytical standard solution of Example 3. This sample was then diluted by a factor of 10 to ensure that the concentration of polyacrylate in the sample would be within the concentration range of the standards of Example 3. To 10.0 ml of the diluted sample were added 1.0 ml of a buffer consisting of 0.062M $KH_2PO_4$ and 0.038M NaOH. The resulting pH was 6.8. Two ml of a $9 \times 10^{-5}$M aqueous solution of pinacyanol chloride were then added. The intensity of the resultant color was measured in a 1 cm cell (light path length) at 600 nm using the spectrophotometer of Example 1. The absorbance was 0.32 absorbance units. Comparison of the absorbance of the diluted sample with the absorbances of polyacrylate standards shown in FIG. 2 indicated a polyacrylate concentration of approximately 0.925 mg/l, which is within the expected 10 percent accuracy range of the test.

EXAMPLE 5

Preparation of Colorimetric Standards—Acrylates With Nile Blue A

Figure 3:
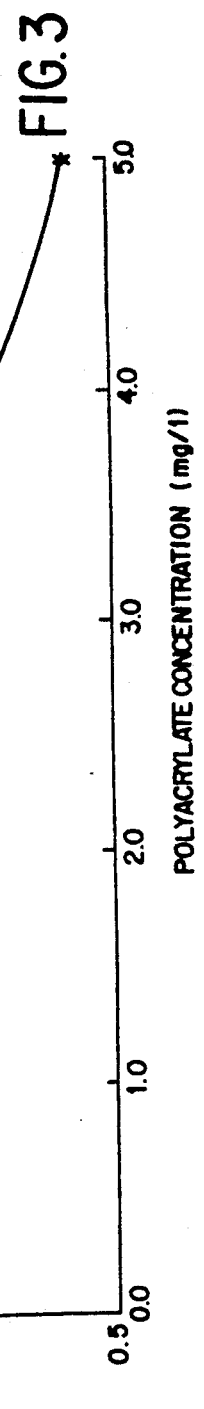
FIG. 3 shows the relationship between absorbance and polyacrylate concentration, as determined by the method described in Example 5.

Polyacrylate standards of 2.0, 4.0 and 5.0 mg/l were prepared by diluting the commercially available 1000 mg/l polyacrylate analytical standard solution of Example 3. To 10.0 ml of each of the above standards and to 10.0 ml deionized water were added 20.0 ml of a buffer solution consisting of 0.0062M $KH_2PO_4$ and 0.0038M NaOH. The resulting pH was 6.8. Two ml of a $5.6 \times 10^{-4}$M aqueous solution of nile blue A were then added to each of these four solutions. The resulting mole ratios of dye molecules to carboxylic acid groups were 7.8, 3.9, 1.0 and 0.0 (deionized water). The intensity of the color developed was measured for each standard at a wavelength of 634 nm in a 1 cm cell (light path length) using the spectrophotometer of Example 1. A calibration curve of absorbance versus polyacrylate concentration was prepared as is shown in FIG. 3.

EXAMPLE 6

Determination of Polyacrylate Concentration In An Industrial Cooling Tower Water Using Nile Blue A A 10.0 ml sample of filtered industrial cooling tower water containing 5.4 mg/l polyacrylate was prepared using the commercially available 1000 mg/l polyacrylate analytical standard solution of Example 3. To this sample were added 20.0 ml of a buffer solution consisting of 0.0062M $KH_2PO_4$ and 0.0038M NaOH. The resulting pH was 6.8. Two ml of a $5.6 \times 10^{-4}$M aqueous solution of nile blue A were than added. The intensity of the color developed was measured in a 1 cm cell (light path length) at 634 nm using the spectrophotometer of Example 1. The absorbance was 0.52 absorbance units. Comparison of the sample absorbance with the absorbances of polyacrylate standards shown in FIG. 3 indicated a polyacrylate concentration of approximately 5.0 mg/l polyacrylate, which is within the expected 10 percent accuracy range of the test.

EXAMPLE 7

Figure 4:
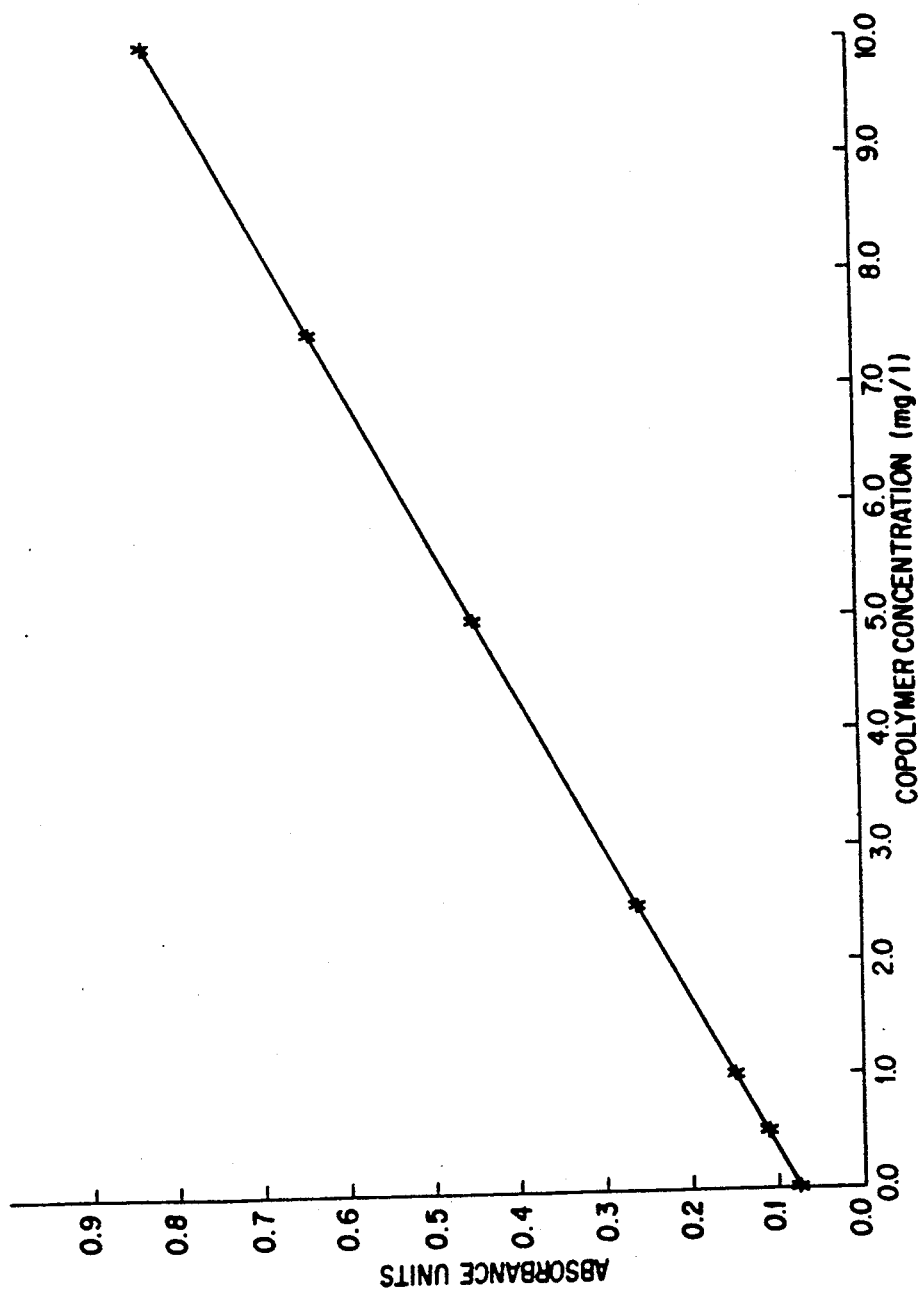
FIG. 4 shows the relationship between absorbance and the concentration of a carboxylic acid/sulfonic acid copolymer, as determined by the method described in Example 7.

Preparation of Colorimetric Standards—Carboxylic Acid/Sulfonic Acid Copolymer With Pinacyanol Chloride Standard solutions containing 1.0, 2.5, 5.0, 7.5 and 10.0 mg/l of an acrylic acid (AA)/2-acrylamido-2-methyl propyl sulfonic acid (AMPS) copolymer having a 60/40 AA/AMPS weight ratio and a molecular weight of 8000 to 10,000 were prepared by diluting the appropriate volume of a 1000 mg/l stock solution of the copolymer with water. To 5.0 ml of each of the standards and to 5.0 ml of deionized water were added 0.05 g of ascorbic acid and 0.50 ml of a buffer solution consisting of 2M chloroacetic acid, 1M sodium chloroacetate, and 60 mg/l thorium. The resulting pH was 2.2. Twelve and one-half ml of a $9 \times 10^{-5}$M aqueous solution of pinacyanol chloride were then added to each of these four solutions. The resulting mole ratios of dye molecules to organic acid groups were 22.0, 11.0, 5.5, 3.71, 2.8 and 0.0 (deionized water). The intensity of the blue color developed was measured at a wavelength of 485 nm in a 50 mm cell (light path length) using the spectrophotometer of Example 1. A calibration curve of absorbance versus copolymer concentration was prepared and is shown as FIG. 4.

EXAMPLE 8

Determination of A Carboxylic Acid/Sulfonic Acid Copolymer Concentration In An Industrial Cooling Tower Water A 5.0 ml sample of filtered industrial cooling tower water containing 10.0 mg/l of the copolymer of Example 7 was prepared. To this sample were added 0.05 g of ascorbic acid and 0.50 ml of a buffer solution consisting of 2M chloroacetic acid, 1M sodium chloroacetate, and 60 mg/l thorium. The resulting pH was 2.2. Twelve and one-half ml of a $9 \times 10^{-5}$M aqueous solution of pinacyanol chloride were then added to the cooling tower water sample. The intensity of the blue color developed was measured at a wavelength of 486 nm in a 50 mm cell (light path length) using the spectrophotometer of Example 1. The absorbance was 0.815 absorbance units. Comparison of the sample absorbance with the absorbance of copolymer standards shown in FIG. 4 indicated a copolymer concentration of approximately 10 mg/l in the cooling tower water, which is within the 10 percent accuracy limit of the test.

Examples 7 and 8 demonstrate that the concentrations of molecules containing both polycarboxylate and sulfonate groups, for example copolymers, can be measured by the instant method. However, if water contains polycarboxylates and sulfonates which are independent of each other (i.e. admixtures rather than copolymers), the concentration of both or either can be measured. First, the instant test method would be conducted at a pH greater than or equal to 3.0, which would allow determination of both the polycarboxylate and sulfonate concentrations. Next, the test method would be conducted at a pH less than 3.0, which would allow determination of the sulfonate concentration alone since, at pH's less than 3.0, polycarboxylates generally do not induce metachromatic charges in dyes. The polycarboxylate concentration could then be determined by difference.

Other uses of this invention will be apparent to those skilled in the art. Though one important use of the invention relates to determining the concentration of polycarboxylate and sulfonate scale inhibitors in boiler or cooling waters, nothing contained herein should be construed as limiting the scope of the invention to applications relating to scale inhibition or to boiler and cooling water applications. In its broadest sense, the instant invention can be used to determine the concentration of polycarboxylates an sulfonates in aqueous systems irrespective of the purpose for which the polycarboxylates and/or sulfonates are used or of the purpose for which the water containing them is used.

What is claimed is:

1. A method for determining the concentration of sulfonate compounds in an aqueous solution comprising:
   (a) adjusting the pH of a portion of said aqueous solution containing sulfonate compounds to a pH less than 3.0;
   (b) adding an effective amount of an aqueous solution of a metachromatic dye to the pH-adjusted portion of Step (a), wherein an effective amount refers to an amount of said dye solution which will, when added to the portion of Step (a), result in a dye to sulfonate group mole ratio between 0.1 and 100.0 in the admixture;
   (c) measuring the absorbance of the admixture resulting from Step (b) at a wavelength between 300 nm and 700 nm;
   (d) comparing the absorbance from Step (c) with absorbances of standard samples containing known concentrations of sulfonate compounds and said effective amount of the dye solution of Step (b), thereby determining the sulfonate concentration of the portion of Step (a).

2. The method of claim 1 wherein said dye is selected from the group consisting of nile blue A, neutral red, safrin O, methylene blue, methyl red, toluidine blue, new methylene blue, quinalizarin, tetrachrome, brilliant blue G, mordant black II and pinacyanol chloride.

3. The method of claim 2 wherein the dye is pinacyanol chloride, wherein the concentration of pinacyanol chloride is from $1 \times 10^{-6}$M and $1 \times 10^{-3}$M, and wherein the absorbance is measured at a wavelength between 480 nm and 490 nm.

4. The method of claim 1 wherein said dye is selected from the group consisting of pinacyanol chloride and nile blue A.

5. The method of claim 1 wherein said pH is between 2.4 and 2.6.

6. The method of claim 1 wherein said portion of an aqueous solution is pretreated by:
   (a) filtering to remove particulates; and/or
   (b) adding a reducing agent to reduce chlorine and/or ferric iron if present, thereby minimizing chlorine and ferric iron interference with the test.

7. The method of claim 1 wherein said portion of an aqueous solution is pretreated by adding an effective amount of thorium to minimize hexametaphosphate interference.

8. The method of claim 1 wherein said portion of an aqueous solution is pretreated by adding an effective amount of an acid to minimize hexametaphosphate interference, wherein said portion is then boiled.

9. The method of claim 1 wherein said sulfonate compounds include water-soluble polysulfonates.

10. The method of claim 1 wherein said sulfonate compounds include copolymers of an unsaturated carboxylic monomer and an unsaturated sulfonate monomer, and wherein the ratios of the respective monomers range from 99:1 to 1:99.

* * * * *